(12) United States Patent
Selander et al.

(10) Patent No.: US 7,154,579 B2
(45) Date of Patent: *Dec. 26, 2006

(54) FRAGRANCE DELIVERY FOR MULTIMEDIA SYSTEMS

(76) Inventors: Raymond K. Selander, 241 E. Hook Rd., Hopewell Junction, NY (US) 12533; Clint Dee Winton Brooks, 4 Grand Pointe Way, Sea Bright, NJ (US) 07760; Lewis Michael Popplewell, 617 Vale Dr., Morganville, NJ (US) 07751

( * ) Notice: Subject to any disclaimer, the term of this patent is extended or adjusted under 35 U.S.C. 154(b) by 111 days.

This patent is subject to a terminal disclaimer.

(21) Appl. No.: 10/950,903

(22) Filed: Sep. 27, 2004

(65) Prior Publication Data

US 2005/0195367 A1  Sep. 8, 2005

Related U.S. Application Data

(63) Continuation-in-part of application No. 10/791,923, filed on Mar. 3, 2004.

(51) Int. Cl.
*G03B 21/32* (2006.01)

(52) U.S. Cl. ......................................... 352/85; 352/40

(58) Field of Classification Search ................. 352/85, 352/40
See application file for complete search history.

(56) References Cited

U.S. PATENT DOCUMENTS

| 4,603,030 | A | * | 7/1986 | McCarthy | 472/57 |
| 4,629,604 | A |   | 12/1986 | Spector |  |
| 5,023,020 | A | * | 6/1991 | Machida et al. | 261/18.1 |
| 5,175,791 | A | * | 12/1992 | Muderlak et al. | 392/390 |
| 5,610,674 | A | * | 3/1997 | Martin | 352/85 |
| 5,647,052 | A | * | 7/1997 | Patel et al. | 392/390 |
| 5,832,320 | A |   | 11/1998 | Wittek |  |
| 5,949,522 | A |   | 9/1999 | Manne |  |
| 6,169,595 | B1 |  | 1/2001 | Manne |  |
| 6,338,818 | B1 |  | 1/2002 | Budman |  |
| 6,536,746 | B1 |  | 3/2003 | Watkins |  |
| 6,602,475 | B1 |  | 8/2003 | Chiao |  |
| 6,654,664 | B1 |  | 11/2003 | Chiao |  |
| 6,744,488 | B1 | * | 6/2004 | Schermerhorn | 352/85 |
| 6,783,084 | B1 | * | 8/2004 | Nelson | 239/307 |
| 6,803,987 | B1 | * | 10/2004 | Manne | 352/85 |
| 2001/0008611 | A1 | * | 7/2001 | Budman | 422/4 |
| 2004/0003812 | A1 |  | 1/2004 | Manne |  |

FOREIGN PATENT DOCUMENTS

| JP | 2000-033120 | 2/2000 |
| JP | 2002-301152 | 10/2002 |
| WO | WO 03/098971 A1 | 11/2003 |

* cited by examiner

*Primary Examiner*—Rodney Fuller (57) ABSTRACT

A system for fragrance sensory stimulation synchronized to a multimedia source connected to an audiovisual display is disclosed. A fragrance generator processes fragrance information from the audiovisual source into a flagrance signal, and a fragrance control system accepts the fragrance signal as an input and generates a control signal and a controlled airflow. In turn, a fragrance delivery system with a plurality of fragrance chemicals in communication with the controlled airflow selectively volatilizes the fragrance chemicals so that a short burst of fragrance is delivered to a user. In certain embodiments, the fragrance delivery system comprises an indexing turret containing a plurality of ports, each containing one fragrance chemical. In another preferred embodiment, a multi-port micro-valve or an array of such valves contains an absorbent material impregnated with a fragrance in each port.

11 Claims, 6 Drawing Sheets

FRAGRANCE DELIVERY FOR MULTIMEDIA SYSTEMS

STATUS OF RELATED APPLICATIONS

This application is a continuation-in-part of U.S. Ser. No. 10/791,923 filed on Mar. 3, 2004. The contents of the Ser. No. 10/791,923 are hereby incorporated by reference.

FIELD OF THE INVENTION

The present invention relates to fragrance delivery systems, and more particularly to fragrance delivery systems that are synchronized with audio and/or visual presentations to add fragrance to a display of sights and/or sounds.

BACKGROUND OF THE INVENTION

The "experience" of audiovisual entertainment has progressed from silent films and monaural recordings to today's visually stunning digital images and advances in sound reproduction such as the "surround sound" found in both commercial theatres and homes. Moreover, current computer-based games and games played on gaming platform employ the same advanced graphics and sound qualities found in film or video. These technologies create an audiovisual "experience" that immerses the user in a film or game like never before, stimulating sight, sound and even tactile sensations through deep bass vibrations provided by subwoofers and tactile feedback provided by some game controllers. There remains, however, one form of sensory perception that is not stimulated—the sense of smell.

Numerous prior art systems have attempted to provide a scent to the environment that compliments or correlates to an audiovisual stimulus. Examples would be the smell of burning rubber coordinating with the screech of tires, or the scent of flowers when a corresponding image appears. Prior art systems have primarily been directed to introducing fragrances to large environments, such as an entire theater. These systems have by and large suffered from the problem that a fragrance will linger long after the coordinating audiovisual input has changed, and may in fact be difficult to replace with another scent as the scenes change, the typical result being a mixture of several fragrances that become an indistinct muddle.

None of these prior art devices, however, provides a useful and commercially viable system for fragrance delivery to enhance an audiovisual presentation. Therefore, there remains a long-felt yet unmet need for providing it would therefore be desirable to provide. It would further be desirable to provide such improvements in a manner that permitted their application across a variety of situations and that permitted their implementation in a cost-effective manner.

SUMMARY OF THE INVENTION

Accordingly, it has now been found that these and other shortcomings of the prior art can be overcome by providing an apparatus for fragrance sensory stimulation that is connected to a multimedia source that has at least one audiovisual signal connected to an audiovisual display, and also has fragrance information synchronized with the audiovisual signal. In preferred embodiments of the present invention, a fragrance generator processes the fragrance information into a fragrance signal and at least one fragrance control system accepts a fragrance signal as an input, and generates a control signal and a controlled airflow. In turn, a fragrance delivery system preferably comprising a plurality of fragrance chemicals in communication with the controlled airflow, selectively volatilizes the fragrance chemicals is so that a short burst of fragrance is sensed by the subject. In certain embodiments, the fragrance delivery system comprises an indexing turret containing a plurality of ports, each port containing one of said plurality of fragrance chemicals. In other preferred embodiment, a multiport micro-valve or array of such valves contains an absorbent material impregnated with a fragrance in each port.

In certain embodiments, the system is constructed as two subassemblies, in which a transmitter is connected to the fragrance generator and a receiver is connected to the fragrance creation system, and the transmitter sends the fragrance signals to the receiver to control the creation of synchronized bursts of fragrance, most preferably provided by a compressor regulated by a microprocessor and including a high-pressure cutoff sensor so that a short burst of pressurized air having a duration of less than five seconds is created. In certain preferred embodiments of the apparatus of the present invention, the fragrance control system is mounted on a user's body, while in other preferred embodiments, the fragrance control system is mounted on a chair. Similarly, in certain preferred embodiments of the apparatus of the present invention, the fragrance delivery system is mounted on a user's body, while in other preferred embodiments, the fragrance control system is mounted on a chair. In other embodiments, a user interface is mounted to the user via an apparatus such as a mask, helmet, headset or earpiece. Alternatively, the interface can be placed adjacent the user, e.g., on a desk, or incorporated into another device such as a steering wheel controller for a game system.

The present invention thus provides a fragrance producing system synchronized to an audiovisual medium that preferably includes a fragrance delivery system for providing a short burst of air containing one of a plurality of fragrance chemicals to an individual user coordinated by receiving and processing a signal contained within the audiovisual medium that has been transmitted to a fragrance creation system in which the signal activates a compressor that selectively volatilizes the fragrance chemical, wherein the plurality of fragrance chemicals are disposed within an apparatus that selectively mixes one of the plurality with a burst of pressurized air generated by said compressor. Most preferably, the signal contained within the audiovisual medium is transmitted via and RF transmitter to an RF receiver connected to the fragrance creation system, and the apparatus that selectively mixes one of the plurality with a burst of pressurized air generated by the compressor comprises a turret with a plurality of ports, and each of the ports includes an absorbent material and a fragrance chemical. Alternatively, the apparatus that selectively mixes one of the plurality with a burst of pressurized air generated by the compressor comprises an array of micro-valves, and each of the micro-valves includes an absorbent material and a fragrance chemical.

Finally, the present invention also discloses methods of synchronizing a fragrance stimulus to a user with one or more audio and visual stimuli by providing a fragrance track to an audiovisual medium to provide a coded signal that correlates to a type of fragrance desired to be released at a pre-determined time, and then determining the divisions within the medium in which fragrance is to be delivered and creating a sequence of fragrances. A device having the requisite number of ports containing a sufficient variety and quantity of fragrance to correspond to the sequence of fragrances is provided and loaded with the fragrance. Next, a signal is processed to activate a compressor and connect the device with an airflow that the correct fragrance chemical is volatilized when a burst of air reaches the fragrance chemical. In certain embodiments, the step of providing a fragrance track comprises programmatic methods direct the system to generate a scent for a pre-determined brief period of time.

DETAILED DESCRIPTION OF THE PREFERRED EMBODIMENTS

The implementation of the present invention is in several preferred embodiments, discussed below, along with several illustrative examples. The embodiments of the invention described below are provided for the purpose of understanding the invention and are not meant to be limiting.

Figure 1:
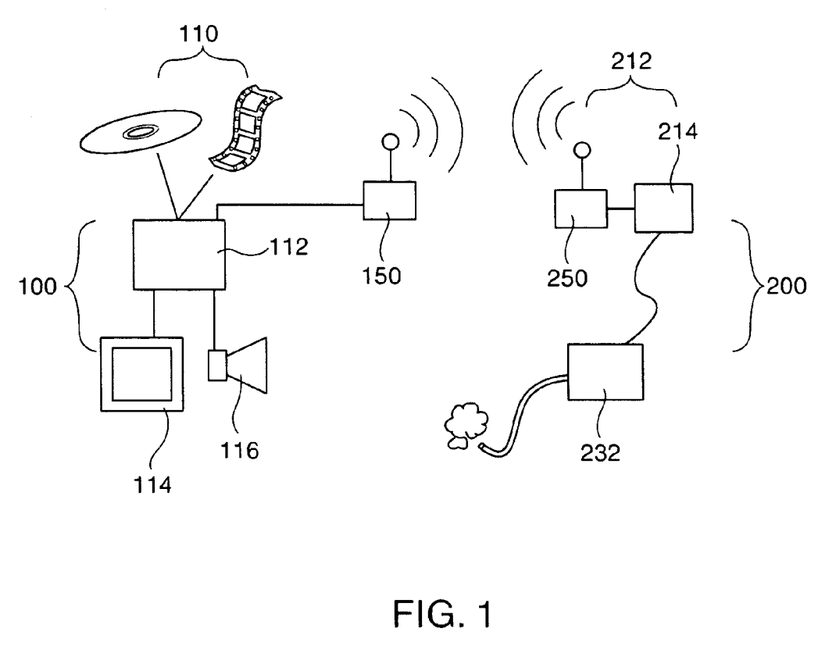
FIG. 1 is a block diagram illustrating a preferred embodiment of the present invention.

Referring now to FIG. 1, a first embodiment of a system employing the present invention is illustrated. There are two main sub-systems that make up this embodiment, namely, the fragrance generator 100 and the fragrance delivery system 200, each of which is discussed in further detail below. In the preferred embodiment illustrated in FIG. 1, the fragrance generator 100 and the delivery system 200 are preferably connected by a wireless system comprising a transmitter 150 and a receiver 250, which are most preferably RF devices, while in other embodiments, such devices and subassemblies can be connected by wires, or integrated into a single unit.

The fragrance generator 100 is comprised of a medium 110 and a media player 112. As known in the art, the medium 110 and media player 112 can be any one of a number of systems, either digital, analog or some combination of such systems, that contains information and converts the information into a signal that can be use for display. Thus, the medium 110 will comprise one or more "tracks" such as a video track, a sound track and, in accordance with the present invention, a fragrance track. The media player 112 will read or process the medium 110 and create signals that can be displayed by devices such as a visual display 114 and an audio display 116. However, in accordance with the present invention, the scent track described above is transmitted to and processed by a fragrance control system 212 that may or may not be integral with the media player 112. As discussed in further detail below and well known in the art, there are a number of systems that contain a scent "medium" (not illustrated in FIG. 1) that can be "played" by the fragrance control system 212 to control the selective release one or more scents in coordination with the information being provided to the visual display 114 and audio display 116. The coordination of emitting various scents during playback of a video, or during the playing of a video game is disclosed in U.S. Pat. No. 6,654,664—Manne and in U.S. Patent Application Publications 2001/0008611 and 2002/0036358, none of which are admitted to be prior art to the present invention.

Figure 2:
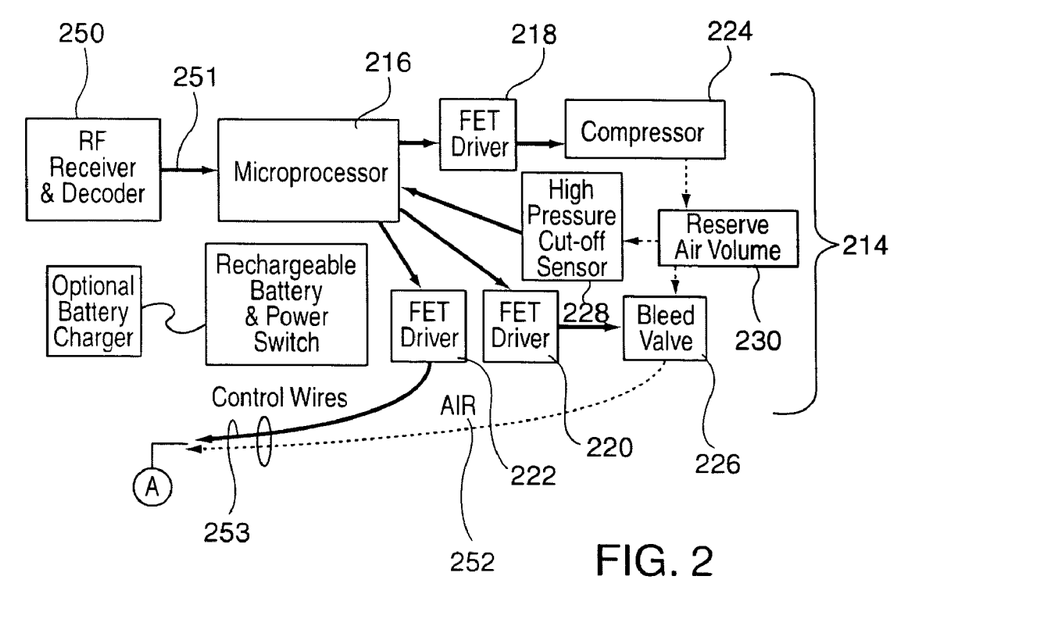
FIG. 2 is a partially schematic, partially perspective view of a preferred embodiment of a fragrance creation system used in the system shown in FIG. 1.

As illustrated in FIG. 1, in certain embodiments of the present invention, the fragrance creation system 212 is divided into two sections, although they may be physically integrated if desired. In accordance with one aspect of the present invention, the fragrance creation system 212 provides short bursts of synchronized fragrances coordinated with audio or visual information on a real-time basis. A first section of the frequency creation system 212 is the fragrance control system 214. Referring now to FIG. 2, a block diagram of one preferred embodiment of a fragrance control system 214 is illustrated. The fragrance control system 214 can be either connected directly to the fragrance generator 100, or as described above, may connected via an RF transmitter 150 and receiver 250 as described above with reference to FIG. 1. In such an embodiment, the RF receiver 250 will include a decoder for RF signal drivers. In any event, a fragrance signal 251 is provided to a microprocessor controller 216, which in turn controls a set of FET drivers 218,220,222 that control, respectively, a compressor 224, a bleed valve 226 and other portions of the device. An additional high-pressure cutoff sensor 228 monitors a reserve air volume 230 and the bleed valve 226. In operation, the microprocessor controller 216 activates the compressor 224. When the upper limit of pressure is achieved, the high pressure cutoff sensor 228 signals the microprocessor to deactivate the compressor, thus creating and maintaining a pressurized system so that when appropriate a short burst of pressurized air is available to be conducted elsewhere in the system. This system may be either be battery powered or wired to a current source. In operation, the microprocessor converts the fragrance signal 251 into a signal that controls a regulated flow of air 252 created by the compressor and a control signal 253, both of which are carried to a fragrance delivery system 232, discussed in detail below with relation to FIG. 3. Thus, the present invention provides precise control of an air pressure reserve that assures immediate and accurately metered delivery of a bolus of scented air that is synchronized with the game, movie or other information, and further that can be provided either as a mixture or a sequential series of scents.

As will be appreciated by those of skill in the art, the system described with relation to FIG. 2 is relatively easy to construct and will be a relatively small-scale unit, thereby permitting devices made in accordance with this aspect of the present invention to be integrated into a compact unit at a relatively low cost to enable economic mass production and widespread implementation. Moreover, such a construction will permit the frequency control system 214 to be constructed in embodiments that can be body-worn, e.g., on a waist belt, or conveniently and unobtrusively mounted to a theatre chair, airline or vehicle passenger seat, or a seat in the home. Further details of the interface to the end user are described and illustrated below with reference to FIGS. 4–10.

Figure 3:
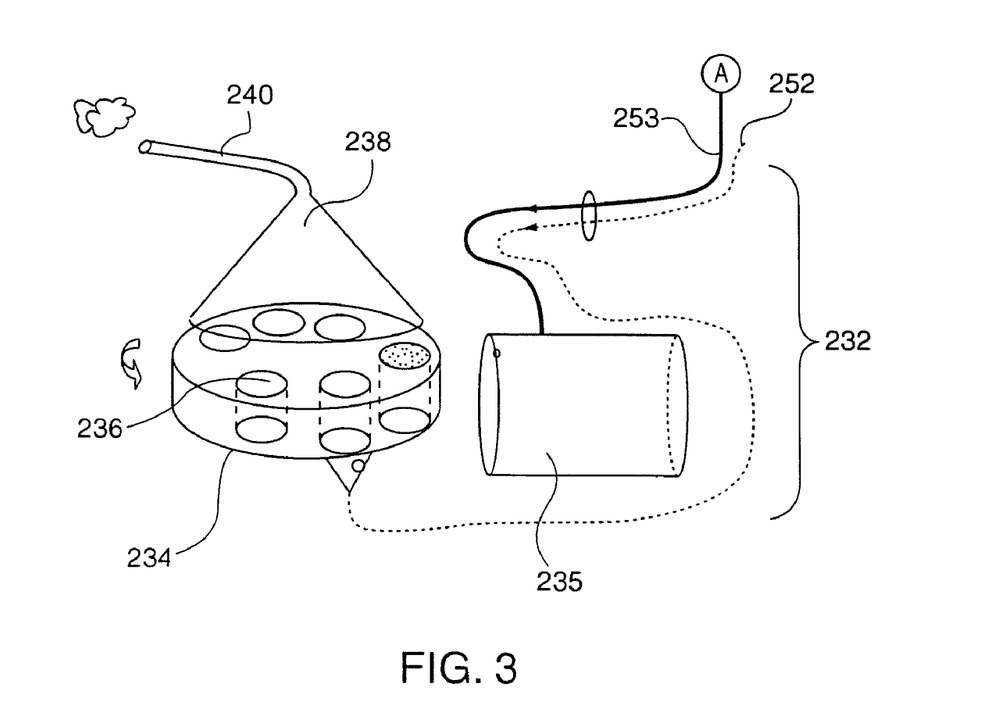
FIG. 3 is a partially schematic, partially perspective view of a preferred embodiment of the delivery creation system used in the system shown in FIG. 1.
Figure 11:
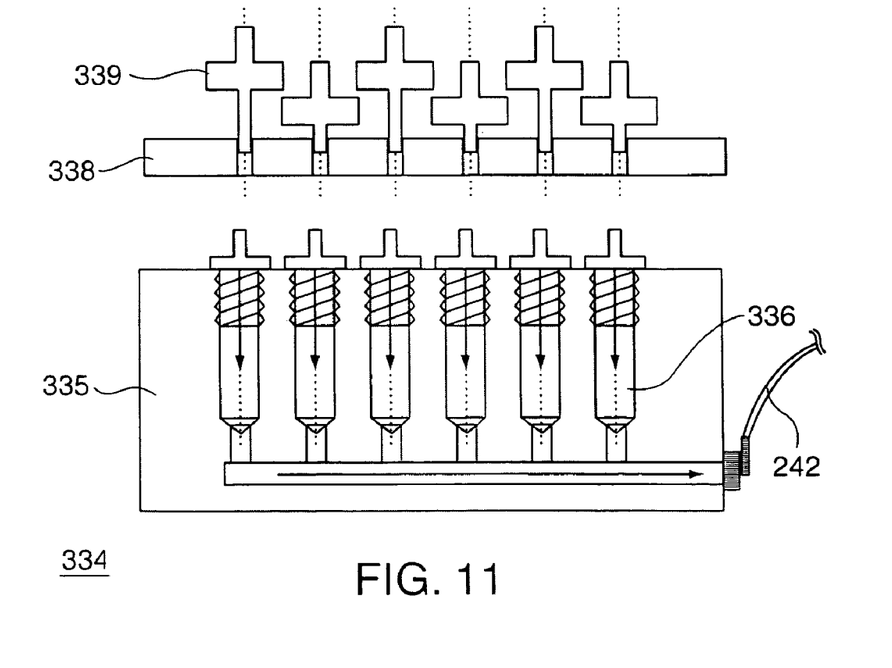
FIG. 11 is a perspective view of a preferred embodiment of delivery creation system in the form of an array of micro-valves.

Referring now to FIG. 3, a partially schematic, partially perspective view of a preferred embodiment of a fragrance delivery system 232 is illustrated. As discussed above with reference to FIG. 2, a controlled flow of air 252 and an electrical signal 253 are carried from the fragrance control system 214. The controlled flow of air 252 is connected via a conduit such that it flows into and through a turret 234 that houses a plurality of fragrance chemicals 236 that are volatilized when the controlled flow of air 252 enters the turret 234. In the preferred embodiment illustrated, the turret 234 includes a plurality of ports or wells 236 that contain an absorbent material that is impregnated or "charged" with a particular scent. The electrical signal 253 controls a solenoid 235 that indexes the turret to a position that corresponds to a particular port 236. Depending upon the use, e.g., commercial or home use, the ports 236 may be accessible so they can be recharged or reloaded with fragrance chemicals, or the entire turret 234 may be a disposable structure that is replaced each time the system is used, or replaced after a specified number of viewings of a film or sessions of game play. In certain other preferred embodiments, the turret 236 can be replaced by an array of micro-valves, each disposed over a port 236 containing fragrance chemical, and the fragrance is volatilized upon opening of the valve by the signal 235 and the passage of the airflow 252 through the open orifice of the valve. As illustrated in FIG. 11, one embodiment of an array of micro-valves 334 includes a valve block 335 that has a series of wells 336 and that is covered by a header 338 (shown in an exploded view) that has a corresponding check valve 339, such as, for one example ⅛ inch (0.125") ID valves P/N 98553-10 available from Cole Parmer. As explained above, each check valve 339 will selectively receive a blast of gas and volatilized fragrance that are then mixed and or sequentially dispersed through the valve block 334 and into the conduit 242 that connects to the nosepiece 240 (not illustrated in FIG. 11). In a highly preferred embodiment of the invention, the array contains a plurality of check valves and electronically controlled pneumatic valves.

Still referring to FIG. 3, as the airflow passes through the turret 236, it is collected by a manifold hood 238 which in turn conducts the airflow, which now carries the selected scent, to a nosepiece 240 or similar structure that directs the fragrance to the nostrils of a single user. The use of a nosepiece and related apparatus to conduct a flow of scented air to a wearer is known in the art, for example, U.S. Patent Application Publication 2004/0003812, which is not admitted to be prior art to the present invention, discloses a portable fragrance control device that releases scent directly into a user's nose via diffusion. The device disclosed is structurally similar to the headsets commonly used for listening and/or speaking. The fragrance delivery system 232 is thus controlled by the signal provided by the fragrance control system 214 and "powered" by the compressor 224 that forms part of that same subsystem. Preferably, the fragrance delivery system 232 is constructed to be lightweight and can be either worn on the body or integrated into the headrest of a chair, but in either case it is preferred that the nosepiece 240 be disposed proximate the wearer's or user's nose so that the fragrance is conducted directly to the individual and does not permeate the environment generally. Details of devices for mounting or placing the nosepiece proximate an end user are described and illustrated below with reference to FIGS. 4–10. Moreover, as mentioned above, it is further desirable that the fragrance delivery system 232 emits short bursts of fragrance at the appropriate synchronized time to enhance the experience of a game, movie or similar audiovisual presentation.

Thus, in operation, those of skill in the art will appreciate that a fundamental requirement of the present invention is that the medium contain an additional "track" that is designed to provide a coded signal that correlates to the type of scent desired to be released at the particular temporal point in the audio or visual presentation. Alternatively, programmatic methods could be employed, e.g., a short algorithm that directs the system to generate a scent upon intervals, e.g., generating short bursts (for example, less than three seconds) of pine scent every thirty seconds during prolonged scenes in an evergreen forest. Such signals, whether part of a "track" or programmed are easily integrated into various forms of media, such as digital discs (CDs, DVDs, etc.), game cartridges, the magnetic tracks found on commercial theatre film, videotape and audiotape, and various other forms of magnetic media. Typically, the numbers of scenes or similar divisions within the medium in which fragrance will make an impact or otherwise be appropriate are identified and a sequence of fragrances is created. A turret or array of valves having the requisite number of ports containing a sufficient variety and quantity of fragrance to correspond to the sequence of fragrances is designed and provided. In operation, the system is loaded with the correct turret or valve array and the user is positioned so the nosepiece described above will transmit fragrance to the wearer in a synchronized fashion. The "fragrance track" provides a signal that is processed to activate the compressor and indexes the turret so that the correct fragrance chemical is volatilized when the burst of air reaches the fragrance chemical.

Figure 4:
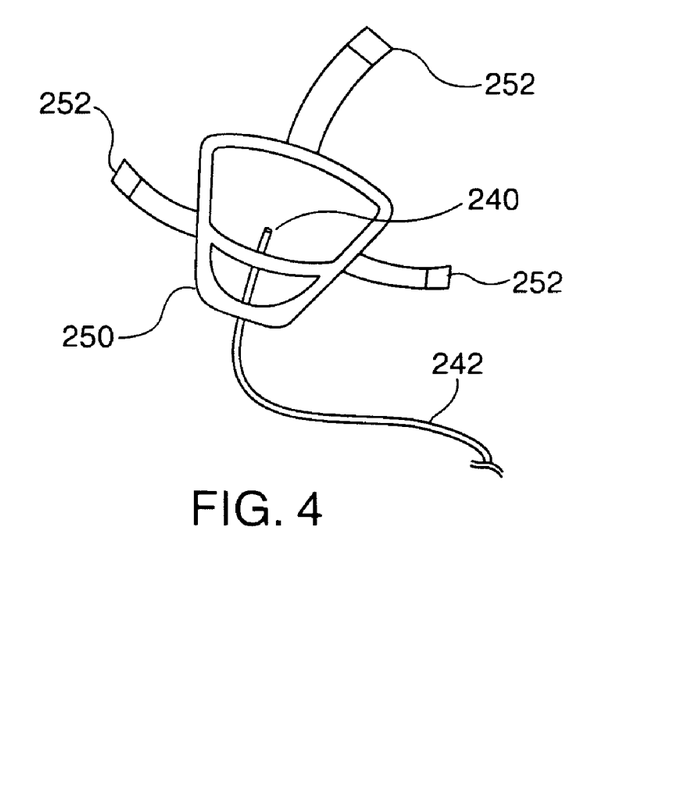
FIG. 4 is a front elevation view of a preferred embodiment of a user interface in the form of a mask.

Referring now to FIGS. 4–8 additional preferred embodiments of apparatus that permit use of the present invention by an end user are shown. As discussed above, in certain embodiments, a nosepiece 240 is provided so that a fragrance is transmitted to an end user. As shown in FIG. 4, in one preferred embodiment, the nosepiece 240 is worn by making it part of a mask 250 that is worn over the front section of the face of a user. A nosepiece conduit 242 conducts both fragrances via one or more conduit tubes, and in some embodiments electrical signals to the nosepiece 240. The mask 250 is preferably provided with head straps 252 so that the mask 250 will remain firmly affixed while the user turns or moves. This embodiment will be particularly adaptable for use with video or computer games involving sports or other action simulations in which the user is immersed in a virtual or near-virtual experience. As know in the art, a face-worn mask can be comprised of a single molded part or make from a more rigid material that is padded with a softer material, e.g., a metal skeleton covered with polyvinyl or EVA foam.

Figure 5:
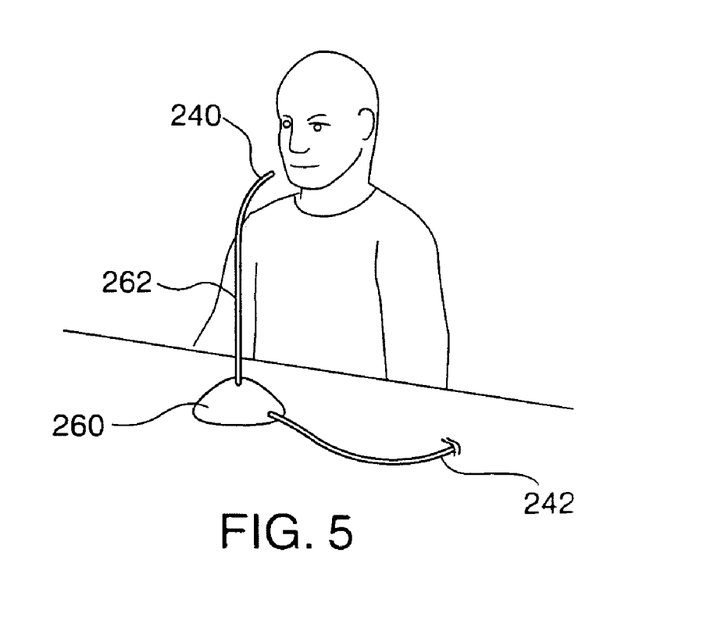
FIG. 5 is a perspective view of a preferred embodiment of a user interface in the form of a "desktop" device.

Referring now to FIG. 5, an alternative embodiment of a device for placing a nosepiece 240 proximate an end user is illustrated. As discussed above with reference to FIG. 4, the nosepiece also comprises a nosepiece conduit 242. In the embodiment illustrated in FIG. 5, the nosepiece 240 is mounted to a stand 260 that is in turn placed on a suitable surface, e.g. a desktop or tabletop. A semi-rigid or bendable stalk 262 extends from the stand 260 and enables the distal end of the nosepiece 240 to be placed near the nose of the end user, as illustrated. Those skilled in the art will understand that the stalk 262 can a separate structure or can simply be a continuation of the conduit 242 if that portion of the device is formed of a material that can be bent and hold a shape, such as molded plastic tubing that is molded around a flexible metal substrate or that has wire embedded within. Alternatively, in certain alternate embodiments it may be desirable for the stalk 262 to be completely rigid.

Figure 6:
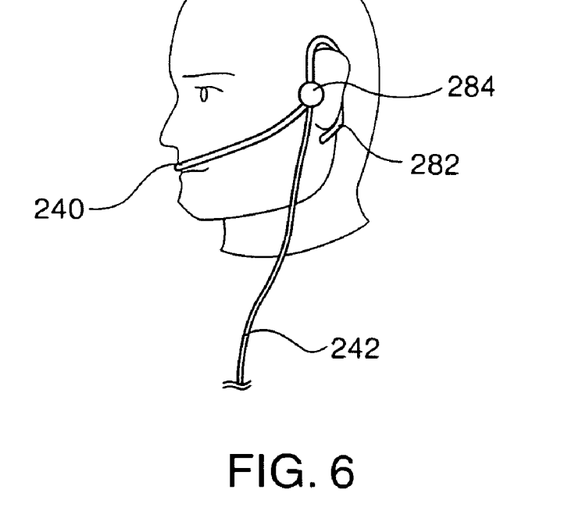
FIG. 6 is a side elevation view of a preferred embodiment of a user interface in the form of a head-mounted device.

An additional embodiment of a device for placing the nosepiece 240 near a user's nostrils is shown in FIG. 6. As illustrated the end user simple wears an earpiece 282 over an ear, and from this structure, the nosepiece 240 extends. This embodiment can further include an earphone 284 attached to the earpiece 282, which will provide additional stability as the user's head moves, and can optionally integrate an earphone to reproduce an audio track. As in the other embodiments discussed herein, the device further includes a conduit 242.

Figure 7:
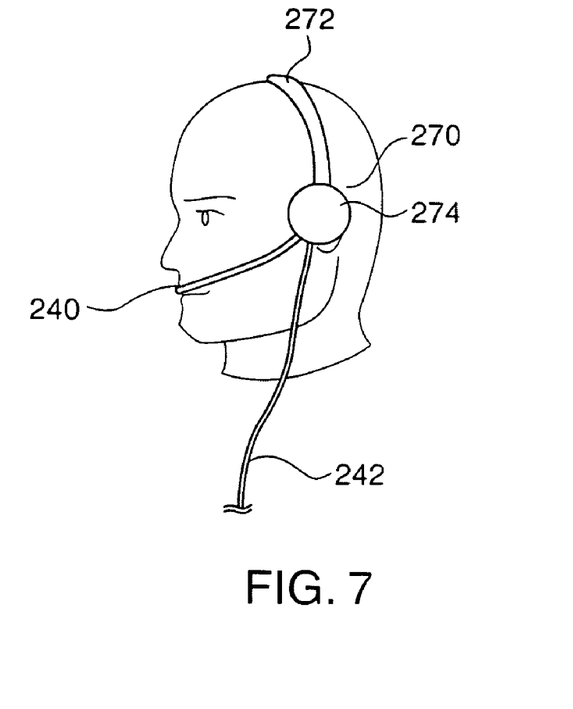
FIG. 7 is a side elevation view of a preferred embodiment of a user interface in the form of an ear-mounted device.

Another embodiment of a device for placing the nosepiece 240 near a user's nostrils is shown in FIG. 7. In this embodiment, the nosepiece 240 extends from a headset 270 that preferably and typically includes a head strap 272. The headset may or may not include one or more headphone speakers 274. In other words, in certain embodiments, a headset structure can be employed without providing sound transmission via the structure surrounding one or both of the ears. As mentioned above with reference to FIG. 4, this embodiment is particularly well suited for action and sports games where the user might tend to undergo a greater degree of head motion than typical in more passive activity such as viewing a movie.

Figure 8:
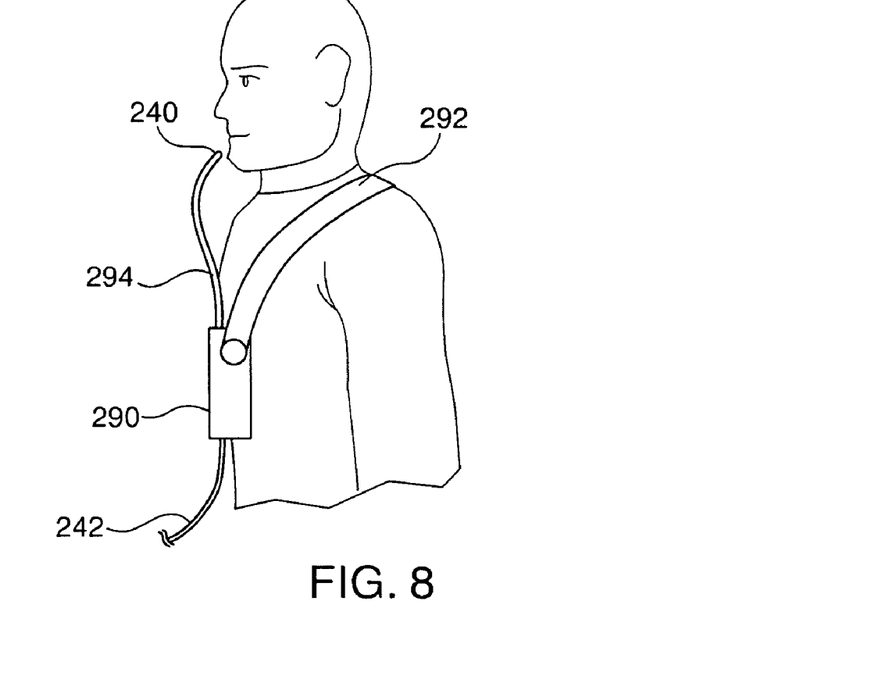
FIG. 8 is a side elevation view of a preferred embodiment of a user interface in the form of a user-worn pendant.

As seen in FIG. 8, another device that permits a user to "wear" the nosepiece 240 is comprised of a pendant 290 that is worn close to the body and preferably attached to the user by a neck strap 292. In this embodiment, the nosepiece 240 again extends from a stalk 294 in the manner discussed above with reference to FIG. 5 only in this embodiment rather than resting on a desk or table, the nosepiece is simply affixed to a pendant 290 that rests against he user's body. The pendant 290 provides an interface with the conduit 244, and could optionally contain additional functions, such as headphone jacks, and in such an embodiment the conduit 242 would further include wires carrying an audio signal.

Figure 9:
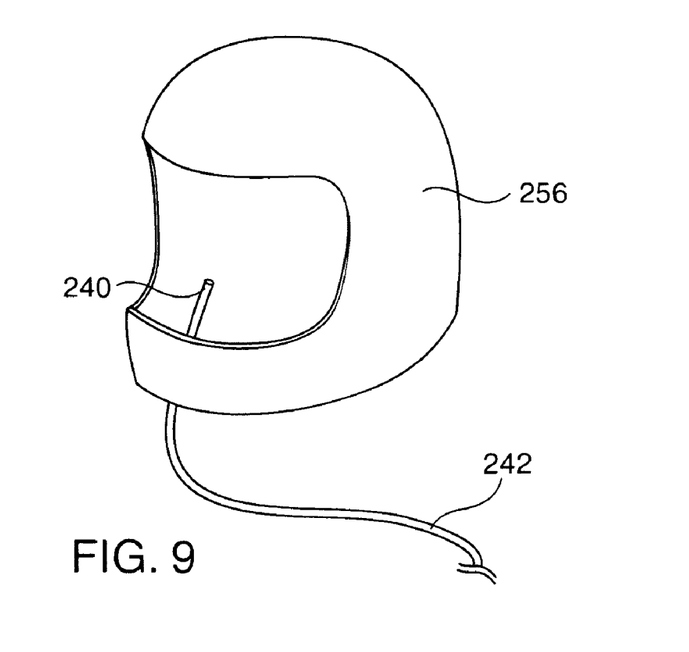
FIG. 9 is a perspective view of a preferred embodiment of a user interface in the form of a helmet.

Referring now to FIG. 9, a user interface in the form of a helmet is illustrated. In this embodiment, a helmet 256 is provided, as is typically known for use with gaming consoles, e.g., to add to the experience of racing games. As is also known, helmets are often employed in "virtual reality" simulators. The helmet 256 incorporates a nosepiece 240. In the embodiment illustrated, the lower edge of the helmet 256 provides a convenient mounting point for the nosepiece 240. In other helmets lacking this lower structure, the nosepiece 240 would be mounted to the helmet and extend along the side of the jawline, as illustrated in FIGS. 6–7. The conduit 242 can, as discussed above, carry both fragrance and audio or other signals, for example if earphones are built into the helmet 256. As discussed above with reference to FIG. 4, and embodiment such as the one illustrated in FIG. 9 is particularly adapted to implementation where the user will undergo significant head movement during game play or other audiovisual experience.

Figure 10:
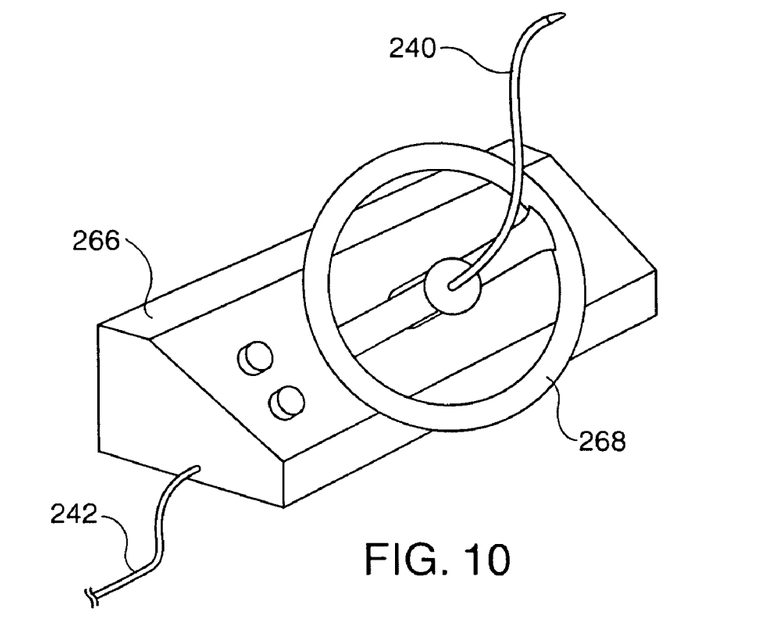
FIG. 10 is a perspective view of a preferred embodiment of a user interface in the form of a steering wheel gaming controller.

Finally, as seen in FIG. 10, a gaming system controller 266 that includes a steering wheel 268 can be adapted for use with the present invention. In this embodiment, as discussed above with reference to FIG. 5, the device is placed on a desk or table near the user and a nosepiece 240 extends upwardly toward the user. As noted above, it is particularly preferable that the nosepiece 240 be constructed so that it can be bent and retain a shape so it can be located in an appropriate position. The conduit 242 carries fragrance to the nosepiece 240 and may optionally include signal wires for game control and/or a power cord.

Upon review of the foregoing, numerous adaptations, modifications, and alterations will occur to the reviewer. These will all be, however, within the spirit of the present invention. Accordingly, reference should be made to the appended claims in order to ascertain the true scope of the present invention.

What is claimed is:

1. An apparatus for fragrance sensory stimulation comprising:
    a multimedia source comprising at least one audiovisual signal connected to an audiovisual display, and fragrance information synchronized with the audiovisual signal;
    a fragrance generator for processing said fragrance information into a fragrance signal;
    at least one fragrance control system that accepts a fragrance signal as an input, and generates a control signal and a controlled airflow; and
    a fragrance delivery system connected to and controlled by the control signal, the fragrance delivery system comprising a plurality of fragrance chemicals in communication with the controlled airflow, a plurality of valves controlled by the control signal and connected to a corresponding plurality of wells wherein the wells, connect to a common delivery conduit,
    whereby at least one of said fragrance chemicals is volatilized and the volatilized fragrance is collected in one of said wells and transferred to the common delivery conduit and sensed by a subject.

2. The apparatus for fragrance sensory stimulation according to claim 1, wherein said plurality of valves comprise check valves and electronically controlled pneumatic valves.

3. The apparatus for fragrance sensory stimulation according to claim 1, further comprising a transmitter connected to the fragrance generator and a receiver connected to the fragrance creation system, whereby the transmitter sends the fragrance signals to the receiver.

4. The apparatus for fragrance sensory stimulation according to claim 1, further comprising a user interface worn by a user.

5. The apparatus for fragrance sensory stimulation according to claim 4, wherein the user interface comprises a mask at least partially surrounding a user's face, and further comprising a scent releasing apparatus disposed near the user's nose.

6. The apparatus for fragrance sensory stimulation according to claim 4, wherein the user interface comprises a helmet at least partially surrounding a user's face, and further comprising a scent releasing apparatus disposed near the user's nose.

7. The apparatus for fragrance sensory stimulation according to claim 4, wherein the user interface comprises an earpiece attached to a user's ear and further comprising a scent releasing apparatus disposed near the user's nose.

8. The apparatus for fragrance sensory stimulation according to claim 4, wherein the user interface comprises a pendant disposed near the user's chest and further comprising a scent releasing apparatus disposed near the user's nose.

9. The apparatus for fragrance sensory stimulation according to claim 1, wherein a user interface is placed adjacent the user and further comprising a scent releasing apparatus disposed near the user's nose.

10. The apparatus of claim 1, wherein the user interface comprises a base and a flexible, bendable stalk.

11. The apparatus of claim 9, wherein the user interface comprises a game controller, a steering wheel connected to the game controller, and a flexible, bendable stalk.

* * * * *